United States Patent [19]

Kensey et al.

[11] Patent Number: 6,015,386
[45] Date of Patent: Jan. 18, 2000

[54] SYSTEM INCLUDING AN IMPLANTABLE DEVICE AND METHODS OF USE FOR DETERMINING BLOOD PRESSURE AND OTHER BLOOD PARAMETERS OF A LIVING BEING

[75] Inventors: Kenneth Kensey, Chester Springs; Harold Clupper, West Chester, both of Pa.

[73] Assignee: BPM Devices, Inc., Exton, Pa.

[21] Appl. No.: 09/073,728

[22] Filed: May 7, 1998

[51] Int. Cl.[7] .................................................. A61N 5/00
[52] U.S. Cl. ...................... 600/486; 128/900; 128/903; 600/481; 600/503
[58] Field of Search ................................ 600/481–504, 600/347–365; 128/897–898, 900, 903

[56] References Cited

U.S. PATENT DOCUMENTS

| 5,720,771 | 2/1998 | Snell | 607/60 |
| 5,791,344 | 8/1998 | Schulman et al. | 600/347 |
| 5,873,837 | 2/1999 | Lieber et al. | 600/800 |

FOREIGN PATENT DOCUMENTS

| 2301826 | 9/1976 | France | G01N 33/16 |
| 2459036 | 1/1981 | France | A61B 5/02 |
| 2823670 | 12/1979 | Germany | A61M 1/03 |
| 4341903 | 6/1995 | Germany | A61B 5/00 |

OTHER PUBLICATIONS

An Article entitled "A Noninvasive Electromagnetic Conductivity Sensor for Biomedical Applications"; Hart, et al., IEEE Transactions On Biochemical Engineering, vol. 35, No. 12, Dec., 1988.

An Article entitled "A System to Aquire and Record Physiological and Behavioral Data Remotely from Nonhuman Primates"; Spelman, et al., IEEE Transactions On Biomedical Engineering, vol. 38, No. 12, Dec., 1991.

Primary Examiner—Cary O'Connor
Assistant Examiner—Michael Astorino
Attorney, Agent, or Firm—Caesar, Rivise, Bernstein, Cohen & Pokotilow, Ltd.

[57] ABSTRACT

A system for monitoring blood pressure within a blood vessel of a living being. The system includes an implantable sensor unit and an associated externally located energy application transceiver. The sensor unit is in the form of a housing including a movable deflection member and a tuned circuit including an inductor coil and a capacitor. The housing surrounds the wall of the blood vessel and includes a wall portion arranged to flatten a portion of the periphery of the blood vessel. The deflection member extends through a slot in the wall portion of the housing for engagement with only the flattened portion of the blood vessel to move in response to the pressure applied to the flattened portion of the blood vessel by the blood. The deflection member includes a ferrite core. The ferrite core is arranged to move with respect to the coil in response to the movement of the deflection member, thereby changing the inductance of the tuned circuit. Electrical energy is provided from the transceiver unit to energize the tuned circuit of the sensor unit, which when energized provides a wireless electrical output signal representative of pressure changes within the blood vessel back to the transceiver. Since the deflection member only engages the flattened portion of the blood vessel the electrical output signal is linear with respect to blood pressure.

27 Claims, 4 Drawing Sheets

SYSTEM INCLUDING AN IMPLANTABLE DEVICE AND METHODS OF USE FOR DETERMINING BLOOD PRESSURE AND OTHER BLOOD PARAMETERS OF A LIVING BEING

SPECIFICATION

This invention relates generally to medical devices and more particularly to systems including implantable devices for monitoring blood pressure and other blood parameters of a living being.

Conventional systems for measuring blood pressure of a living being typically require a pressurized occlusive cuff and means to monitor and analyze the resulting Korotkoff sound or the oscillometric pressure variations. A few ambulatory systems are available, but such systems cannot collect data continuously, not retrieve the pulsatile waveform. Another type of blood pressure monitoring system makes use of a device which is disposed in contact with the skin of the person located over the radial artery. This type of system measures the force resulting from a partially flattened radial artery. However, since this type of system makes its measurements through the intervening tissue and is sensitive to motion and exertion of the subject, less than optimum performance would be expected. Thus, while short-term transcutaneous pulse recording may be possible, it would appear to suffer from inaccuracy and drift due to local tissue accommodation and/or possible nonlinear and viscoelastic effects of the blood vessel tissue.

While direct access to the interior of the blood vessel via an arterial puncture may provide a viable technique for short term blood pressure determination applications, it would appear not feasible for a series of long-term measurements. Moreover, transcutaneous or percutaneous access to the interior of the blood vessel to measure/monitor the pressure therein carries with it various health risks inherent in any arterial puncture, particularly where wires have to extend through the arterial wall and the intervening tissues for an extended period of time.

Other types of implantable devices for monitoring the blood pressure of a living being, e.g., a human or animal, have been disclosed in the patent literature. See for example, U.S. Pat. No. 3,149,492 (Weinberg), U.S. Pat. No. 3,189,023 (Salz et al.), U.S. Pat. No. 4,190,057 (Hill et al.), U.S. Pat. No. 4,256,094 (Kapp et al.); and U.S. Pat. No. 4,926,875 (Rabinovitz et al.). While these devices may be generally suitable for their intended purposes, the still leave much to be desired from various standpoints. For example, the Salz et al. patent requires that electrical conductors (wires) extend out through the body of the being from an implanted unit extending about the blood vessel. While in the context of the application for which the device of the Salz et al. was designed, i.e., to monitor the blood pressure of an astronaut during a rocket launch, the use transcutaneously extending wires or leads may be acceptable, it never the less provides a drawback from the standpoint of restriction of mobility, resistance to infection, discomfort. The Weinberg, Kapp et al., and Rabinovitz et al. patents all exhibit the same limitation, i.e., the necessity of leads or wires extending from the implanted device through the skin to the recording or measuring device.

One approach taken by the prior art to eliminate the necessity for wires to extend through the skin is to apply the blood pressure sensor externally. The following United States Letters Patent disclose externally applied blood pressure monitors: U.S. Pat. No. 4,830,017 (Perry et al.) U.S. Pat. No. 4,836,213 (Wenzel et al.), U.S. Pat. No. 4,987,900 (Eckerle et al.), U.S. Pat. No. 4,924,871 (Honeyager), U.S. Pat. No. 5,183,050 (Kawamura), U.S. Pat. No. 5,158,091 (Butterfield et al.), U.S. Pat. No. 5,238,000 (Niwa), U.S. Pat. No. 5,406,952 (Barnes et al.), U.S. Pat. No. 5,439,001 (Butterfield et al.), and U.S. Pat. No. 5,439,002 (Narimatsu). A wrist mounted blood pressure monitor identified as a "Compact Wrist Blood Pressure Monitor" has been offered by Omron under the model designation HEM-605. It would appear that externally applied blood pressure sensor-based systems would suffer from the same drawbacks as mentioned above, e.g., sensitivity to motion and exertion of the subject, inaccuracy and drift due to local tissue accommodation and/or possible nonlinear and viscoelastic effects of the tissues involved.

Numerous patents have been issued disclosing various means for monitoring intracranial pressure by means of an implant to sense such pressure and provide a wireless signal representative thereof to some externally located means. Such intracranial pressure monitoring systems do not appear suitable for determining blood pressure. The following are United States Letters Patents relating to intracranial pressure monitoring systems: U.S. Pat. No. 3,853,117 (Murr), U.S. Pat. No. 3,943,915 (Severson), U.S. Pat. No. 3,977,391 (Fleischmann), U.S. Pat. No. 4,003,141 (LeRoy), U.S. Pat. No. 4,014,319 (Favre), U.S. Pat. No. 4,026,276 (Chubbuck), U.S. Pat. No. 4,062,354 (Taylor et al.), U.S. Pat. No. 4,114,606 (Seylar), U.S. Pat. No. 4,127,110 (Bullara), U.S. Pat. No. 4,186,749 (Fryer), U.S. Pat. No. 4,206,761 (Cosman), U.S. Pat. No. 4,206,762 (Cosman), U.S. Pat. No. 4,246,908 (Inagaki et al.), U.S. Pat. No. 4,265,252 (Chubbuck et al.), U.S. Pat. No. 4,281,667 (Cosman), U.S. Pat. No. 4,354,506 (Sakaguchi et al.), U.S. Pat. No. 4,378,809 (Cosman), U.S. Pat. No. 4,471,786 (Inagaki et al.), U.S. Pat. No. 4,494,411 (Koschke et al.), U.S. Pat. No. 4,593,703 (Cosman), U.S. Pat. No. 4,653,508 (Cosman), U.S. Pat. No. 4,660,568 (Cosman), U.S. Pat. No. 4,676,255 (Cosman), U.S. Pat. No. 4,738,267 (Lazorthes et al.), U.S. Pat. No. 4,926,696 (Haritonidis et al.), U.S. Pat. No. 5,018,529 (Tenerz et al.) and U.S. Pat. No. 5,317,917 (Dufour).

Several publications have disclosed various types of technology potentially useful for monitoring blood pressure, such as "High-Efficiency Coupling-Insensitive Transcutaneous Power and Data Transmission Via an Inductive Link," IEEE Transactions on Biomedical Engineering, July 1990; "A system to Acquire and Record Physiological and Behavioral Data Remotely from Nonhuman Primates," IEEE Trans on Biomed Eng, December 1991; "A Noninvasive Electromagnetic Conductivity Sensor for Biomedical Applications," IEEE Trans on Biomed Eng., December 1988; and "Noninvasive Blood Pressure Recording and the Genesis of Korotkoff Sound," Drezewiecki, et al., Chapter 8, Handbook of Bioengineering, Vol. 1. The technology described by Drezewiecki requires a superficial artery, such as the radial artery, which is supported by a bony structure just proximal to the wrist. An external force is applied to the artery sufficient to distort and partially flatten the artery. The force profile is then measured to give a blood pressure reading. Although non-invasive, this approach appears to lack stability and requires complicated servo mechanisms to locate and flatten the artery. Long term unattended measurements do not appear possible. A basic problem with this approach is that it requires use of an external means, such as a cuff, to apply pressure through tissue to effect a measurement.

OBJECTS OF THE INVENTION

Accordingly, it is a general object of this invention to provide a system for determining and/or monitoring a living being's blood pressure which overcomes the disadvantages of the prior art.

It is a further object of this invention to provide a system including an implantable device for determining and/or monitoring a living being's blood pressure.

It is a further object of this invention to provide a system including an implantable device for determining and/or monitoring a living being's blood pressure which is simple in construction.

It is a further object of this invention to provide a system including an implantable device for determining and/or monitoring a living being's blood pressure and an externally located energy application/transceiver unit.

It is still a further object of this invention to provide a blood pressure detecting/monitoring system making use of an implantable sensor/transducer unit which is biocompatible, suitable for long-term use, and which doesn't present any danger to the patient.

It is yet a further object of this invention to provide a system suitable for ambulatory monitoring of the blood pressure of a living being.

SUMMARY OF THE INVENTION

These and other objects of this invention are achieved by providing apparatus and methods of use for monitoring the pressure within a blood vessel of a living being (e.g., a human). The system comprises a sensor/transducer unit and an associated energy application/transceiver unit. The sensor/transducer unit is adapted to be implanted within the body of the being, e.g., at the radial artery immediately proximally of the wrist. The energy application/transceiver unit is arranged to be located externally of the body of the being but adjacent the situs of the implanted sensor/transducer unit to selectively provide energy to the sensor/transducer unit to activate that unit and to receive wireless signals representative of the being's blood pressure therefrom.

The sensor/transducer unit includes a housing for surrounding at least a portion of the wall of the blood vessel when implanted. A portion of the housing serves to flatten a portion of the blood vessel's periphery. A deflection member, e.g., a probe having a ferrite core mounted on it, is located within the housing and is movable with respect thereto in response to pressure changes within the blood vessel. The deflection member is coupled to passive energy responsive means, e.g., an inductor coil so that movement of the core effects a change in the inductance of the coil located within the housing. The energy responsive means is arranged for providing an output signal, e.g, a wireless electromagnetic signal, representative of pressure changes within the blood vessel in response to energy applied thereto by the externally located energy applicator/transceiver unit. The energy applicator/transceiver unit is arranged to pick up or receive the wireless electromagnetic signal.

BRIEF DESCRIPTION OF THE DRAWINGS

Other objects and many of the attendant advantages of this invention will readily be appreciated as the same becomes better understood by reference to the following detailed description when considered in connection with the accompanying drawings wherein.

DETAILED DESCRIPTION OF THE PREFERRED EMBODIMENT

Figure 1:
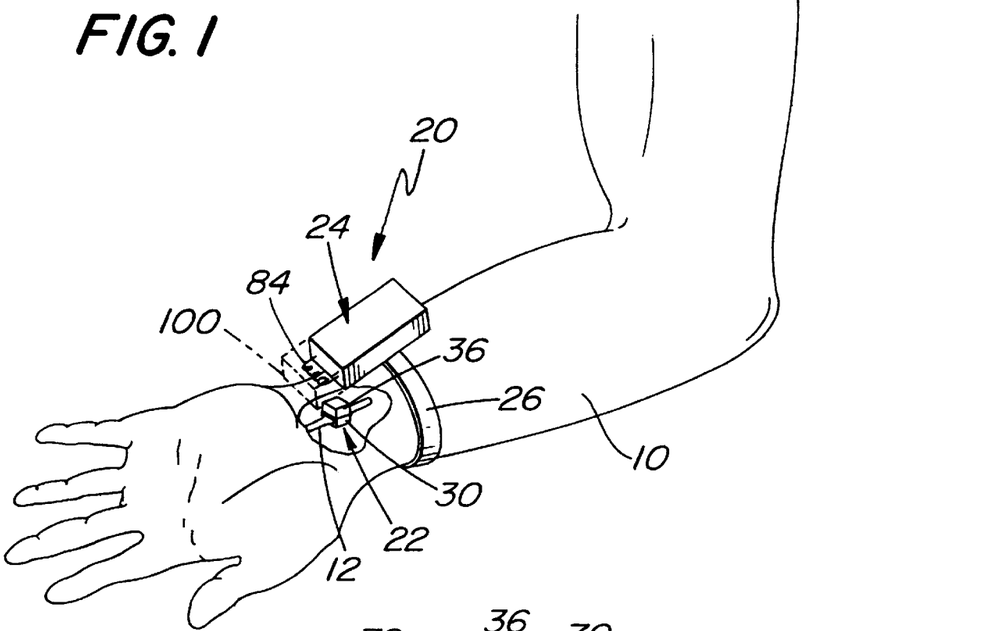
FIG. 1 is an isometric view of an blood pressure system including an implantable sensor/transducer unit and an externally located energy application/transceiver unit shown in a typical application determining and/or monitoring the blood pressure of a living being, e.g., a human being.

Referring now to the drawing where like reference numerals refer to like parts there is shown at 20 in FIG. 1 a system constructed in accordance with this invention for monitoring or determining the blood pressure in a blood vessel of a living being. The system 20 basically includes an implantable sensor/transducer unit 22 and an associated energy application or transceiver unit 24. The sensor/transducer unit 22 is a passive device, i.e., it does not include any internal power source. It is arranged to be implanted at any suitable location within the body of the being, e.g., just below the skin and underlying tissue within the subject's forearm 10 immediately proximally of the bony structure of the wrist so that it can be coupled to the radial artery 12, like shown in FIGS. 1 and 2.

The transceiver unit 24 is arranged to be located externally of the body of the subject but proximate the implanted sensor/transducer unit to wirelessly transmit electromagnetic energy to that unit 22. Upon receipt of that energy the sensor/transducer 22 unit becomes energized, whereupon it determines the subject's blood pressure within the radial artery and produces an electromagnetic output signal is indicative thereof. The electromagnetic output signal is detected wirelessly by the externally located transceiver unit 24. That unit is preferably a small, portable device which is arranged for ready transportation so that the subject can determine/monitor his/her blood pressure whenever and wherever desired. In accordance with a preferred embodiment of the invention the transceiver 24 includes a strap or band 26 enabling it to be held in position on the body of the subject over the location of the implanted sensor/transducer unit 22. The transceiver unit 24 may also include means, e.g., a microprocessor and associated software, for effecting automatic operation to determine/monitor the patient's blood pressure at some predetermined time or at predetermined intervals. Moreover, the transceiver unit 24 may include means for recording the blood pressure data and/or for transmitting such data to some remote location.

The construction of the sensor/transducer unit 22 is best seen in FIGS. 2–5. Thus, as can be seen therein that unit basically comprises a housing 28 in which the various components of the unit are located. Two passive electrical components making up a tuned L-C circuit and several mechanical components associated with that circuit and coupling that circuit to the radial artery are located within the housing. The housing is formed of any biocompatible material, e.g., a plastic, and includes a bottom section 30 having a rectangular channel 32 located therein, a pivotable door 34 closing the channel 32, and a top section 36 enclosing the various electrical and mechanical components of the unit. The bottom section is a generally U-shaped member having a planar bottom wall 38, a planar side wall 40, and a planar top wall 42. The channel 32 is defined between the bottom wall 38, side wall 40 and top wall 42. An ear 44 (FIG. 5) projects downward from the outer surface of the bottom wall 38 contiguous with the entrance of the channel 32. The ear serves as a portion of a hinge pivotally connecting the door 34 to the bottom wall 38. The door 34 basically comprises a planar member having an upper flange 46 and a lower flange 48. A pivot pin 50 (FIG. 5) extends through an opening in the lower flange 48 and a corresponding opening in the ear 44 to enable the door to be pivoted with respect to the housing from an open position (not shown) to a closed position (shown in FIG. 5). In the open position the channel 32 is exposed to enable the housing to be placed on the radial artery 12 so that the radial artery is located within the channel 32. Once the radial artery is in place the door 34 is closed to its closed position, like that shown in FIGS. 2 and 5, whereupon the sensor/transducer unit 22 is locked in place with respect thereto.

Figure 2:
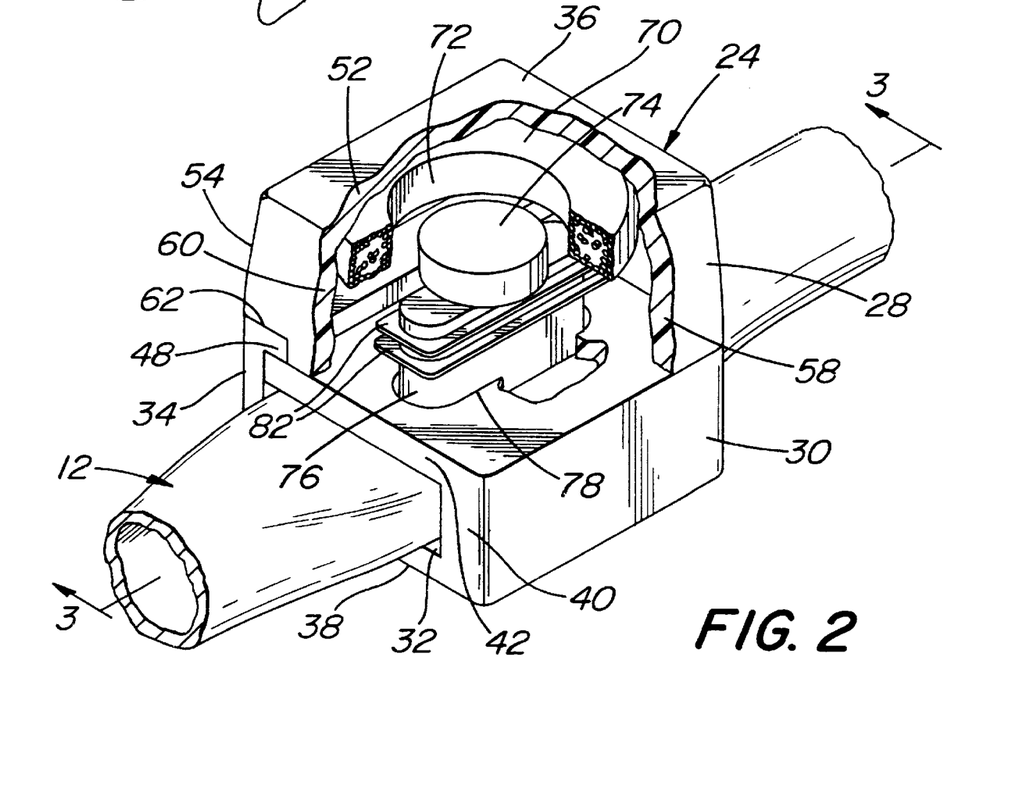
FIG. 2 is an enlarged isometric view, partially broken away, of the implantable sensor/transducer portion of the system shown in FIG. 1 and a portion of the blood vessel, e.g., the radial artery, to which it is coupled.
Figure 3:
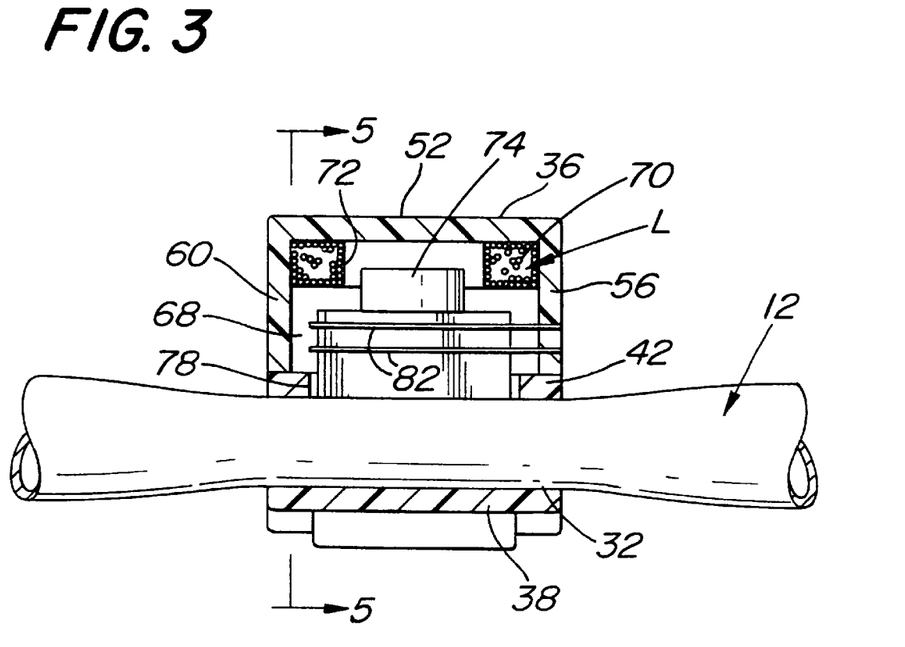
FIG. 3 is a sectional view taken along line 3—3 of FIG. 2.
Figure 4:
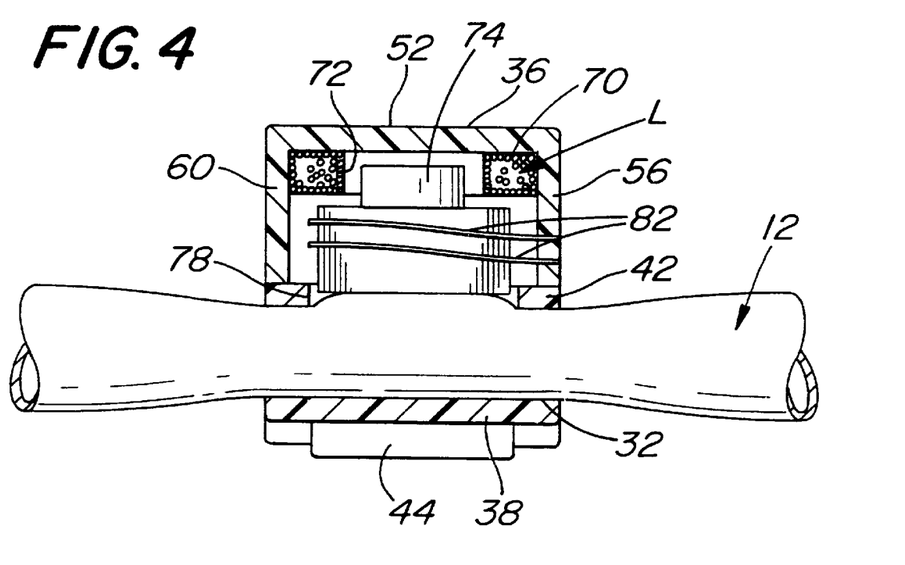
FIG. 4 is sectional view like that of FIG. 3 but showing the sensor/transducer detecting a higher blood pressure within the blood vessel than that shown in FIG. 3.
Figure 5:
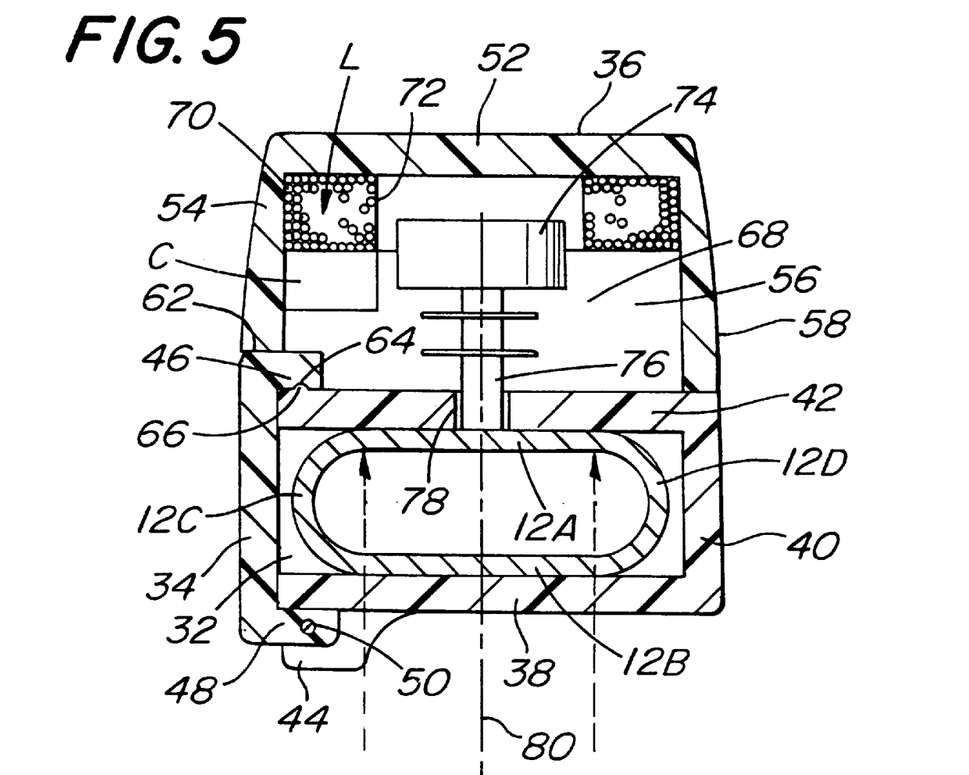
FIG. 5 is a sectional view taken along line 5—5 of FIG. 3.

The top section 36 is a rectangular hollow member having a top wall 52 and four peripheral side walls 54 (FIGS. 2 and 5), 56 (FIGS. 3–5), 58 (FIGS. 2 and 5), and 60 (FIG. 2). The top wall 52 is planar, as are the side walls, except that they each flare out slightly in the downward direction. The bottom edge of each of the side walls 56, 58 and 60 is joined, e.g., adhesively secured, to the periphery of the top wall 42 of the bottom section 30. The height of the side wall 54 is less than that of the sidewalls 56, 58 and 60 to form a slot 62 between it and the edge of the wall 42 of the bottom section 30. The slot 62 is arranged to closely receive the upper flange 46 of the door 34 when the door is closed. In order to hold the door in the closed position to prevent it from accidentally reopening and allowing the sensor/transducer unit to become disengaged from the radial artery a small dimple 64 (FIG. 5) is provided in the inner surface of the flange 46 of the door 34. A mating projection 66 is located on the top surface of the top wall 42.

The hollow interior 68 of the upper section 36, i.e., the portion bounded by the upper section's walls 52, 54, 56, 58 and 60 and the lower section's top wall 42 serves to hold the various electrical components of the sensor/transducer unit 22. The electrical components constitute an inductor L and a capacitor C (see FIG. 5). The inductor L is formed as a coil 70 of multiple loops of wire forming a ring having a central opening 72 therein. The inductor L is of the variable type and includes a cylindrical ferrite core 74. As known in the art, the presence of a ferrite core has the property of greatly increasing the inductance of an inductor. The core 74 is mounted on a deflectable member or probe 76 which is arranged to engage a flattened portion of the radial artery whose position is a function of the blood pressure within the vessel being monitored, e.g., the radial artery. Thus, the resonant frequency of the L-C tuned circuit will respond to pressure variations within that vessel.

Figure 7:
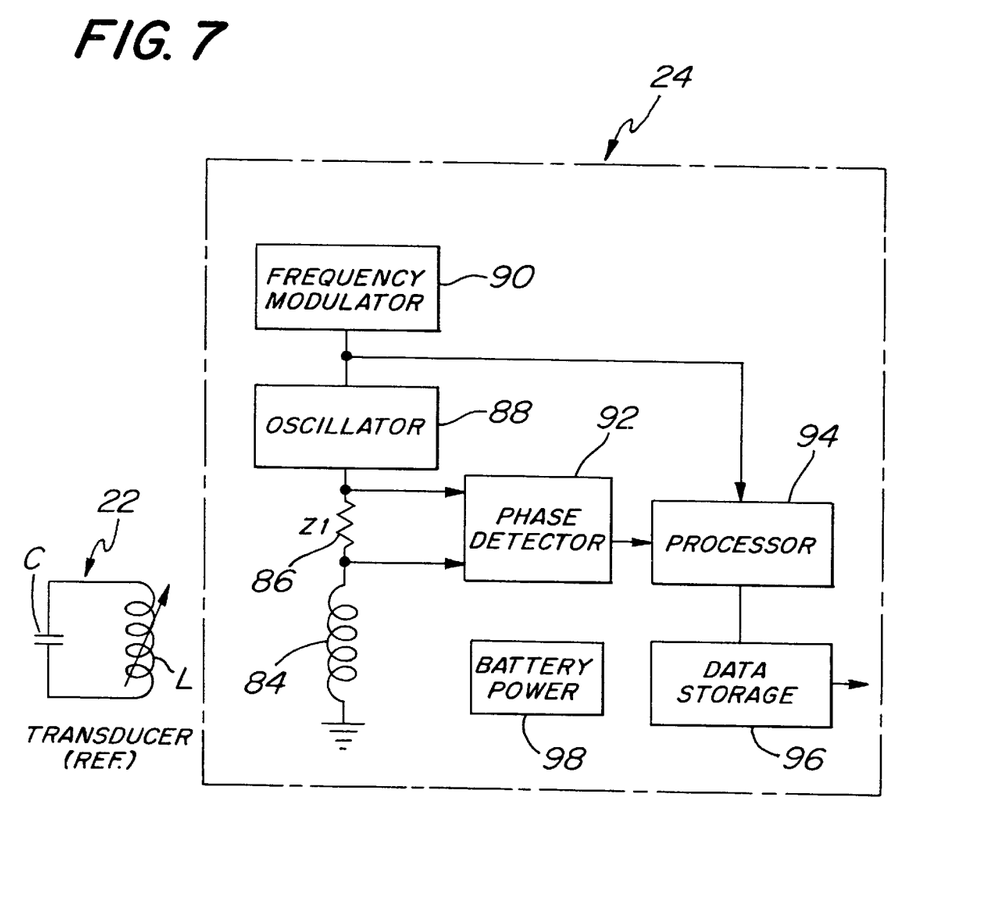
FIG. 7 is a electrical diagram partially in block diagram form and partially in schematic form showing the construction of the electrical components making up the sensor/transducer unit and the energy application/transceiver unit.

The coil 70 is mounted within the interior 68 of the upper section of the housing so that its central opening 72 is located within the center of the housing. In the embodiment shown the coil is secured to the inner surface of the top wall 52. The ferrite core 74 is mounted on the probe 76 and is axially aligned with the central axis 80 (FIG. 5) of the coil 70. The probe 76 is movable along the central axis 80 to move the ferrite core 74 within the central opening 72 in the coil 70. The capacitor C is mounted below the coil 70 and is electrically connected to it to form a parallel resonant L-C circuit as shown in FIG. 7. The variable inductor L and the fixed capacitor C form the sensor of the sensor/transducer unit 22. The resonant frequency of the sensor circuit is determined by the values of the inductance and capacitance. In this instance, the value of the capacitance is held constant and the value of the inductance is varied as a function of the internal vessel pressure by the movable ferrite core 74. It is also possible to vary the value of the capacitance in a similar manner.

As will be described in more detail later the resonant frequency is detected outside the body of the subject by means of the transceiver 24, and in particular, a frequency swept radio frequency oscillator (to be described later) forming a portion of the transceiver.

The probe 76 is preferably of a flattened oval cross section to fit closely within an elongated slot 78 (to be described later) in the top wall 42 of the lower section 30 of the housing. The elongated slot 78 is centered on the axis 80 of the coil 70 and probe 76. The elongated slot 78 includes a longitudinal or major axis which is oriented aligned with the longitudinal axis of the radial artery 12 (See FIG. 2). For adult humans it is contemplated that the width of the probe 76, i.e., its dimension measured along its minor axis, to be on the order of 0.5 mm.

In order to constrain the motion of the probe 76 and the attached ferrite core 74 to a relatively linear motion and to provide a restoring force, plural, e.g., two, compliant flat springs 82 are used. The flat springs 82 are mounted in a parallelogram arrangement as shown in FIGS. 2–5, with one end fixed to the interior surface of the wall 56 of the upper portion 36 of the housing and the other end fixed to the opposite end of the flattened oval shaped probe 76.

As mentioned earlier and as best seen in FIG. 5, the channel 32 of the housing of the sensor/transducer unit 22 serves to flatten at least one portion of the radial artery 12, but not all of it. In particular, the channel's top wall 42 flattens one portion 12A of the radial artery, while the opposed channel wall 38 flattens a portion 12B of that artery on the opposite side from the portion 12A. The remaining portions of the artery 12C and 12D are unconstrained and thus assume an arcuate shape. The flattening of the portions 12A and 12B of the artery wall relieves those portions of stress resulting from the elasticity of the artery wall at those locations. Thus, at those locations the stress on the artery wall is proportional to the vessel's blood pressure P, alone. It is over a portion of the flattened area 12A that the stress is measured by the sensor/transducer 22 of this invention to provide an output signal proportional to the blood pressure within the vessel. In particular, the planar wall portion 42 contiguous with the periphery of the elongated slot 78 prevents the artery wall portion 12A from bulging out except for the part of the area 12A which is bounded by the slot 78. It is this unconstrained vessel area which the lower end of the probe 76 makes contact with to detect any deflection (movement) thereof. While the portion of the radial artery within the area bounded by the slot 78 is effectively unconstrained, e.g., it can bulge out (See FIG. 4), the contiguous surrounding area 12A is flattened by the planar wall 42. Thus, any stress due to the elasticity of the artery wall within the area bounded by the slot 78 becomes negligible so that the stress detected within the area bounded by the slot 78 is solely a function of the blood pressure P within the artery. In accordance with a preferred embodiment of this invention the channel 34 flattens a portion of the radial artery to approximately 2.1 mm for an adult so that such flattening approximates a reduction in cross-sectional area of about 30 to 35 percent. Such a reduction is believed to have a negligible effect on blood flow and should not result in any adverse effect on the patient.

Figure 6:
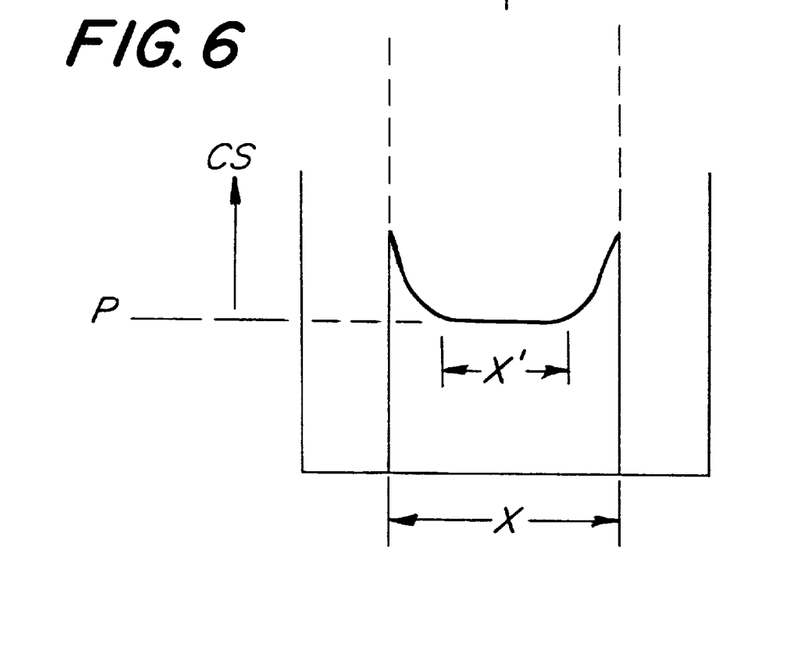
FIG. 6 is a graph showing the distribution of contact stress over the length of the portion of the blood vessel which is deformed by the sensor/transducer unit.

FIG. 6 is a graph showing the distribution of contact stress over the length of the portion of the blood vessel. As can be seen in this figure, contact stress CS is plotted on the ordinate versus the length of the blood vessel plotted on the abscissa. The portion X of the graph represents the portion of the length of the blood vessel 12 which is deformed by the sensor/transducer unit, e.g., the housing. At the center of the deformation there is a plateau X' wherein the stress due to the elastic vessel wall becomes negligible. Over this length, X', the stress is proportional to the vessel pressure, P, alone. It is over this area that the stress is measured by the probe and associated components of the sensor/transducer unit 22. In particular, the blood pressure induced stress at the flattened portion 12A of the artery within the bounds of the slot 78 is detected by the engaging probe 76, i.e., the probe is moved along axis 80 to a position representative of the blood pressure. This action carries the ferrite core 74 along that axis, thus changing its position with respect to the coil 70, whereupon the coil's inductance is varied. The change of inductance is detected by means of the L-C tuned circuit, the resonant frequency of which is determined by the resulting value of the inductance L and the capacitance C. In particular, upon receipt of the electromagnetic energy from the transceiver 24, the tuned L-C circuit resonates at its resonant frequency to produce an output electromagnetic, e.g., electrical, signal representative of the blood pressure. This output signal is detected wirelessly by the externally located transceiver 24 as well as described hereinafter.

The details of the electrical operation of the system 20 will now be described with reference to FIG. 7. That figure is a simplified schematic diagram of the tuned L-C circuit making up the sensor/transducer 22, and of the various electrical components making up the externally located transceiver 24. Being a simplified schematic some components and connections are not shown, but are well within the skill of the art, e.g., can be constructed in accordance with the teaching of various the prior art patents identified above or other conventional technology.

In the exemplary embodiment shown, the electrical components making up the transceiver unit 24 basically comprise an energizer/search coil 84, a complex impedance 86, an oscillator 88, a frequency modulator 90, a phase detector 92, a processor 94, a data storage device 96, and an internal power source, e.g., battery 98. The processor may be either analog or digital, with a digital microprocessor being preferred. The software for controlling the operation of the processor is arranged to be stored in associated storage means (not shown) forming a part of the transceiver unit.

The energizer/search coil 84 is located under a cover 100 (shown in phantom in FIG. 1) forming a portion of the transceiver's housing, and is connected on one side to ground. The other side of the coil 84 is connected to one side of the complex impedance 86. The other side of that impedance is connected to the output of the oscillator 88. The input to the oscillator 88 is provided by the frequency modulator 90. The phase detector 92 has two inputs connected across the impedance 86. The output of the phase detector is provided as one input to the processor 94. The other input of the processor is provided from the output of the frequency modulator 90. The output of the processor 94 is provided to the data storage device 96. That device can be of any construction to provide an output signal representative of the blood pressure detected/monitored by the sensor/transducer to any other suitable means, e.g., a printer, modem, etc. The battery 98 provides electrical power to the various components making up the transceiver unit 24.

Operation of the system 20 is as follows. When a blood pressure reading is desired the transceiver unit is mounted on the subjects' body (if not already in place) so that the transceiver's coil 84 is disposed over and oriented properly with respect to the coil of the implanted sensor/transducer unit. A switch (not shown) is provided in the transceiver, which when activated either manually or under control of the processor 94 (such as could occur if the system 20 is arranged for automatic or remote control operation), causes the transceiver's oscillator 88 to provide an alternating current signal via the complex impedance 86 to the coil 84. The oscillator 88 is swept in frequency over a small range by the frequency modulator 90. The coil 84, when energized, generates an electromagnetic signal or field. Since the transceiver 24 is located over the sensor/transducer unit, e.g., at the surface of the skin of the subject, the electromagnetic field is coupled to the coil 70 of the sensor/transducer unit 22. This action effectively "energizes" the sensor/transducer unit 22. When the field generated by coil 84 of the transceiver equals the resonant frequency of the L-C circuit of the sensor/transducer unit 22, the reflected impedance (i.e., the "output" signal of the sensor/transducer unit 22) causes a change in the impedance of the coil 84. This impedance change manifests itself as change in phase shift across the complex impedance 86 which is detected by the phase detector 92 and sent on to the processor 94. The processor 94 also receives a modulation signal from the frequency modulator 90 which has defined the oscillator frequency sweep. By detecting the timing of the output signal, i.e., the phase pulse, from the phase detector 92 and comparing it with the modulation signal from the frequency modulator 90, the processor 94 determines the frequency at which the transducer is resonating and hence indicates the detected blood pressure. The output signal representing the detected/monitored blood pressure is preferably stored in the data storage device 96 for later downloading for display and analysis. Alternatively, or in addition, the transceiver unit 24 may include means for displaying and/or printing out the data representing the subject's blood pressure.

To achieve an accurate representation of the pulsatile blood pressure waveform the frequency of the system 20 is preferably swept at a 30–40 Hz rate. The processor 94 is arranged to average several pulsatile cycles and determine the diastolic and systolic pressures for storage. Because of the high memory requirements, the discrete waveform data may not be recorded continuously. In particular, it is contemplated that several cycles of pulsatile waveforms will be recorded intermittently in accordance with a predetermined stored or received diagnostic routine. Alternatively, the discrete waveforms may be saved when certain limits are exceeded. Patient feedback by means of audible or tactile alarms (not shown) may also be included in the transceiver unit 24.

As mentioned above the tuned L-C can make use of a variable capacitor in lieu of a variable inductor to alter the resonant frequency of the tuned circuit in response to movement of the flattened portion of the vessel wall. In such a case the capacitor is coupled to the flattened portion of the vessel wall so that movement of that portion changes the capacitance of the capacitor. It is also contemplated that both the inductor and capacitor can be variable and both be coupled to the flattened portion of the vessel wall. In fact, the means for providing an output signal representative of movement of the flattened portion of the vessel wall (and hence the extant blood pressure) need not be a tuned electrical circuit. Thus, the signal can be provided by other types of devices for providing a tissue permeable output signal responsive to vessel wall position. Examples of such signals may be sound (such as ultrasound), radiation, or other types of electromagnetic radiation (such as visible light, infrared light, etc.). Moreover, this invention contemplates mechanizing the transducer as a transponder which receives power at one frequency and transmits the blood pressure data at another frequency.

As should be appreciated by those skilled in the art from the foregoing, the subject invention provides various advantages over the prior art, particularly for applications requiring blood pressure determination and/or monitoring over extended periods of time. For example, with the subject invention measurements may be made continuously without disturbing the patient, e.g., there is no pressure cuff required to be placed on the patient's arm. Moreover the system can provide better accuracy than standard cuff methods. Since a portion of the system is implanted and fixed with respect to the blood vessel, motion artifacts, should be minimal. Further still, since the system of this invention is capable of providing data whenever required, e.g., periodically or non-periodically over an extended period of time, the system can provide better data for the management of various conditions, e.g., high blood pressure, in patients.

Since the system utilizes a passive sensor/transducer unit, i.e., one that does not require any implanted power source, such as a battery, the sensor/transducer unit can be left in place indefinitely, if desired. Also the system effectively eliminates observer bias and enables the pulsatile waveform to be retrieved readily, showing reflections and other artifacts.

The subject system can be used to reduce the frequency of visits to a health care provider for blood pressure determinations. In fact, since a portion of the system is implanted, while the other portion is readily transportable, the need for visits to a health care provider's office for a pressure determination can be eliminated entirely. Thus, for example, the system of this invention may be used in the workplace to gather data while the subject is at work.

While, as noted above, the implanted sensor/transducer unit does flatten out a portion of the artery (or other blood vessel) to which it is coupled in order to provide an accurate representation of existing blood pressure, the total area of the artery which is reduced is approximately only 30–35%, an insignificant amount from the standpoint of potential hazard to the patient. Moreover, since the artery is not punctured or otherwise penetrated by the sensor/transducer, the risk of a blood-born infection or other adverse effects on the patient is minimized, if not eliminated.

As should be appreciated by those skilled in the art the treatment of various diseases or physiological conditions may greatly benefit from the acquisition of reliable data indicative of a person's blood pressure taken over an extended period of time. Data regarding other physiological factors, such as the patient's temperature, heart rate, muscle tension, sleep patterns, perspiration, and tremors, if correlated to the monitored blood pressure are likely to provide additional information facilitating the diagnosis and/or treatment of diseases or physiological conditions. Moreover, various environmental factors, such as the time of the measurement(s), the ambient noise, ambient temperature, ambient light, air movement, etc., may also play a role in a person's blood pressure. Thus, it is contemplated that the subject invention be used in a system monitoring one or more of the foregoing physiological and/or environmental factors, whereupon the data regarding the patient's blood pressure and one or more of the other factors may be correlated to provide valuable information from which a diagnosis or treatment may be developed. Further still, the system may make use of various alarms or other means to indicate when one or more predetermined factors has been exceeded.

It should be noted that while the subject invention has been discussed with reference to monitoring/determining the subject's blood pressure, the teachings of this invention can be implemented to determine/monitor other blood pressure parameters or parameters of other fluids flowing through vessels, ducts, lumens in the body of a living being, providing that such parameters can be calculated or determined in response to the position of an unconstrained flattened portion of the wall of the vessel, duct or lumen.

Without further elaboration the foregoing will so fully illustrate my invention that others may, by applying current or future knowledge, adopt the same for use under various conditions of service.

What is claimed is:

1. A blood pressure monitoring system, said system arranged to be used in a living being, the being having a blood vessel in which blood flows and which exhibits a pressure, said system being arranged for monitoring the blood pressure within the blood vessel of the living being and comprising a passive sensor unit and an associated energy application unit, said sensor unit being adapted to be implanted within the body of the being, said energy application unit being adapted to be located externally of the body of the being for wireless transmission of energy waves to said sensor unit, said sensor unit being constructed to at least partially surround the wall of the blood vessel to cause a first portion of the blood vessel to assume a flat shape and to enable the flat shaped portion of the blood vessel to move to a position in response to the blood pressure within the blood vessel, said sensor unit operating in response to said energy applied to said sensor unit by said externally located energy application unit to provide a wireless output signal indicative of the position of the flat shaped portion of the blood vessel, whereupon the blood pressure within the blood vessel may be determined.

2. The system of claim 1 wherein said sensor unit comprises a housing, a deflection member, and passive energy responsive means, said housing being adapted to surround the wall of the blood vessel and including a wall portion arranged to flatten a portion of the periphery of the blood vessel to form said flat shaped portion, said deflection member being arranged to engage the flat shaped portion of the blood vessel and movable with respect to the housing in response to the pressure applied to the flat shaped portion of the blood vessel by the blood therein, said deflection member being coupled to said passive energy responsive means, said passive energy responsive means being responsive to the position of said deflection member for providing said wireless output signal.

3. The system of claim 2 wherein said deflection member is confined to engage only the flat shaped portion of the blood vessel, whereupon said output signal varies linearly with blood pressure changes.

4. The system of claim 1 wherein said energy waves comprise electromagnetic energy.

5. The system of claim 4 wherein said electromagnetic energy comprises electrical energy.

6. The system of claim 1 wherein said output signal comprises an electrical signal having a frequency indicative of the blood pressure.

7. The system of claim 6 wherein said sensor unit comprises a tuned circuit including an inductor and a capacitor.

8. The system of claim 7 wherein said energy application unit includes an inductor for receipt of said output signal.

9. The system of claim 2 wherein said wall of said housing is flat and includes a slot therein through which said deflection member extends for engagement with the flat shaped portion of the blood vessel.

10. The system of claim 7 wherein sensor unit additionally comprises a ferrite core connected to said deflection member and movable therewith, said inductor comprising a coil mounted within said housing so that said core can be extended into and out of said coil in response to movement of said deflection member.

11. The system of claim 2 additionally comprising biasing means for biasing the position of said deflection member.

12. The system of claim 11 wherein said biasing means comprises a leaf spring connected to said housing.

13. A method for monitoring the blood pressure within a blood vessel of a living being, the being having a blood vessel in which blood flows and which exhibits a pressure, said method comprising the steps of:

(a) providing an energy application unit located externally of the body of the being;

(b) implanting a sensor unit within the body of the being to engage a portion of the blood vessel to cause the portion of the blood vessel to assume a flat shape, while allowing the flat shaped portion of the blood vessel to move to a position in response to the blood pressure within the blood vessel of the being; and (c) monitoring the movement of said flat shaped portion of the blood vessel in response to energy applied wirelessly from outside the body of the being.

14. The method of claim 13 wherein said method additionally comprises the step of:

d. providing a wireless output signal from said sensor unit, said wireless output signal being indicative of the blood pressure monitored by said sensor unit.

15. The method of claim 14 wherein said unit comprises a movable deflection member and wherein said method additionally comprising the step of:

e. providing said output signal in response to the position of said movable deflection member.

16. The method of claim 15 additionally comprising the step of:

f. confining said deflection member to engage only the flat shaped portion of the blood vessel, whereupon said output signal varies linearly with blood pressure changes.

17. The method of claim 16 wherein said energy applied to said unit is electromagnetic energy.

18. The method of claim 17 wherein said electromagnetic energy comprises electrical energy.

19. The method of claim 13 wherein said output signal comprises an electrical signal having a frequency indicative of the blood pressure.

20. The method of claim 13 wherein said system is operated to provide blood pressure readings over an extended period of time.

21. The method of claim 13 additionally comprising the step of acquiring data regarding at least one other physiological factors of the patient and correlating such a factor to the monitored blood pressure.

22. The method of claim 13 additionally comprising the step of acquiring data regarding at least one environmental factors and correlating such a factor to the monitored blood pressure.

23. The method of claim 21 wherein said at least one other physiological factor is selected from the group consisting of the being's temperature, heart rate, muscle tension, sleep patterns, perspiration, and tremors.

24. The method of claim 22 wherein said at least one environmental factor is selected from the group consisting of the time of the measurement, the ambient noise, ambient temperature, ambient light, and air movement.

25. The method of claim 13 additionally comprising the step of providing an alarm signal if the monitored blood pressure exceeds a predetermined level.

26. The method of claim 22 additionally comprising the step of providing an alarm signal if the monitored blood pressure and/or the at least one other physiological factor exceeds a predetermined level.

27. The method of claim 23 additionally comprising the step of providing an alarm signal if the monitored blood pressure and/or the at least one environmental factor exceeds a predetermined level.

* * * * *